United States Patent [19]
Fujioka

[11] Patent Number: 4,549,816
[45] Date of Patent: Oct. 29, 1985

[54] APPARATUS FOR MEASURING MELTING AND BOILING POINTS OF GAS

[75] Inventor: Koji Fujioka, Sapporo, Japan

[73] Assignee: Hoxan Corporation, Sapporo, Japan

[21] Appl. No.: 531,262

[22] Filed: Sep. 12, 1983

[30] Foreign Application Priority Data

Oct. 13, 1982 [JP] Japan .......................... 57-154879[U]
Mar. 30, 1983 [JP] Japan ............................ 58-46149[U]

[51] Int. Cl.⁴ ............................................. G01N 25/02
[52] U.S. Cl. .................................. 374/27; 165/104.21; 165/11.1; 374/157
[58] Field of Search ....................... 374/27, 24, 25, 16, 374/157; 165/61, 104.21

[56] References Cited
U.S. PATENT DOCUMENTS

| | | | |
|---|---|---|---|
| 2,671,342 | 3/1954 | Kapff | 374/24 X |
| 3,216,239 | 11/1965 | Talbot et al. | 374/27 |
| 3,440,865 | 4/1969 | Gamson | 374/27 X |
| 3,589,168 | 6/1971 | Hankison | 374/24 |
| 4,428,684 | 1/1984 | Kuraoka | 374/25 |

FOREIGN PATENT DOCUMENTS

| | | | |
|---|---|---|---|
| 0057596 | 8/1982 | European Pat. Off. | 374/16 |
| 2000859 | 1/1979 | United Kingdom | 374/16 |
| 2077405 | 12/1981 | United Kingdom | 374/16 |

*Primary Examiner*—Daniel M. Yasich
*Attorney, Agent, or Firm*—George B. Oujevolk

[57] ABSTRACT

An apparatus for measuring the melting and boiling points of gas has a heat insulating tank, an inner tank within the insulating tank, a sample cell within the inner tank with a sample gas temperature measuring system. A piping system is provided having a heating route and a cooling route. The heating route has a heating flow rate control valve and a heating heat exchanged heated by a heating source connected in series with the control valve. The cooling route has a cooling flow rate control valve and a cooling heat exchanger connected in series with the cooling flow rate contorl valve. The heating and cooling routes are in parallel. The heating source for heating the heat exchanger has a Joule-Thomson expansion valve while the cooling part for cooling the cooling heat exchanger is coupled to a compressor for compressing and supplying a refrigerant such as Freon.

3 Claims, 5 Drawing Figures

APPARATUS FOR MEASURING MELTING AND BOILING POINTS OF GAS

BACKGROUND OF THE INVENTION

This invention relates to an improvement in an apparatus for measuring the melting point and boiling point of gas to obtain the purity and the mixture ratio of sample gases.

A variety of methods of measuring, for example, with a gas chromatograph or the like the purity of a sample gas such as benzene or the mixture ratio of several gases in mixed gases are heretofore carried out, but its measuring operation is complicated and the apparatus for measuring them is disadvantageously considerably expensive.

Accordingly, the inventor of the present invention has already proposed an appratus for accurately measuring the melting point of sample gas by utilizing the fact that the melting point and the boiling point of the gas vary according to the amount of impurities contained in the sample gas and that the melting point and the boiling point of the gas exhibit predetermined value in accordance with the mixture ratio of the mixed gases.

SUMMARY OF THE INVENTION

Accordingly, an object of this invention is to provide an apparatus for measuring the melting point and the boiling point of gas which can simplify the configuration heretofore proposed by the inventor by integrating the heating source and the cooling source with an advantageous piping structure, thereby reducing the cost of the apparatus so as to eliminate the disadvantages of the prior apparatus and which can further constructing the heat medium source suitably, thereby accelerating the measurement.

The above and other related objects and features of the invention will be apparent from a reading of the following description of the disclosure found in the accompanying drawings and the novelty thereof pointed out in the appended claims.

DESCRIPTION OF THE PREFERRED EMBODIMENTS

Figure 1:
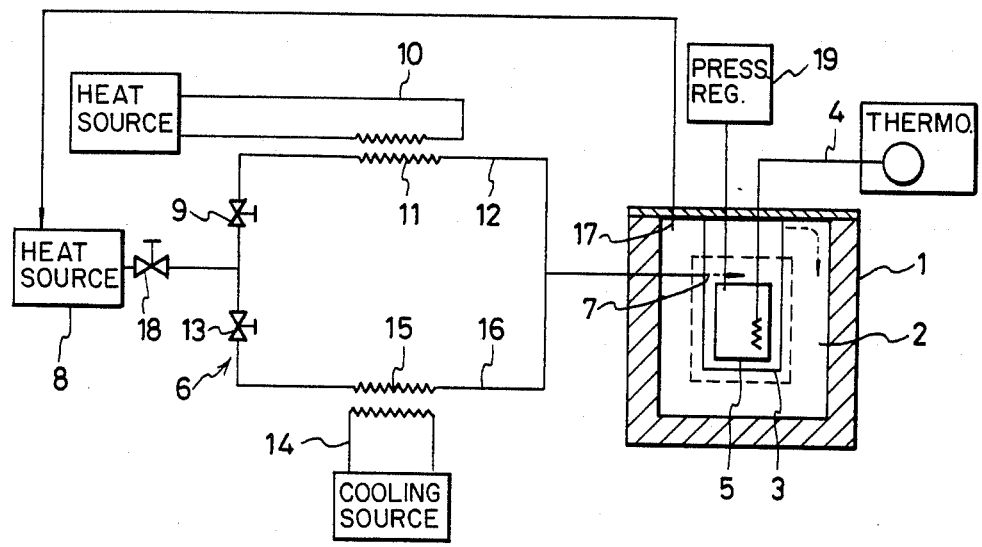
FIG. 1 is an explanatory piping diagram partly cut out of a machine heretofore proposed for measuring the melting point and the boiling point of gas.

To properly understand the present invention, it is first necessary to understand the apparatus heretofore proposed by the present inventor. In the proposed apparatus, an inner tank 3 is, as shown in FIG. 1, internally provided within a heat insulating tank 1 through a passage 2 for flowing heat medium. In the tank 3 is contained a sample cell 5 which has a temperature measuring system 4 for measuring the temperature of the sample gas charged in the tank 3, thereby opening the outlet 7 of a piping system 6 provided for controlling the temperature of the tank 3. The piping system 13 consists of a heating pipe route 12 which connects a heating flow rate control valve 9 and a heating heat exchanger 11 heated by a heating source 10 in series with each other and a cooling pipe route 16 which connects a cooling flow rate control valve 13 and a cooling heat exchanger 15, cooled by a cooling source 14, in parallel with a heat medium source 8 for gas or the like of heat medium. Further, the tank 3 is connected to the passage 2, and the outlet 17 of the passage 2 provided at the tank 1 is connected to the heat medium source 8 thereby constituting a circulating system. Reference numeral 18 designates a control valve provided at the inlet side of the piping system 6, and 19 is a pressure regulator which is connected to the sample cell 5.

In the apparatus just described, the temperature of the heat medium which is flowed from the piping system 6 into the tank 3 is controlled by controlling the openings of the valves 9 and 13, and the melting point and the boiling point can be accurately measured by raising or lowering the temperature of the sample gas to a desired value.

However, in the proposed apparatus, there is a disadvantageous in that the heating source 10 and the cooling source 14 are separately provided in the piping system 6 so that the size of the apparatus is increased and the cost of the apparatus is not inexpensive.

Figure 2:
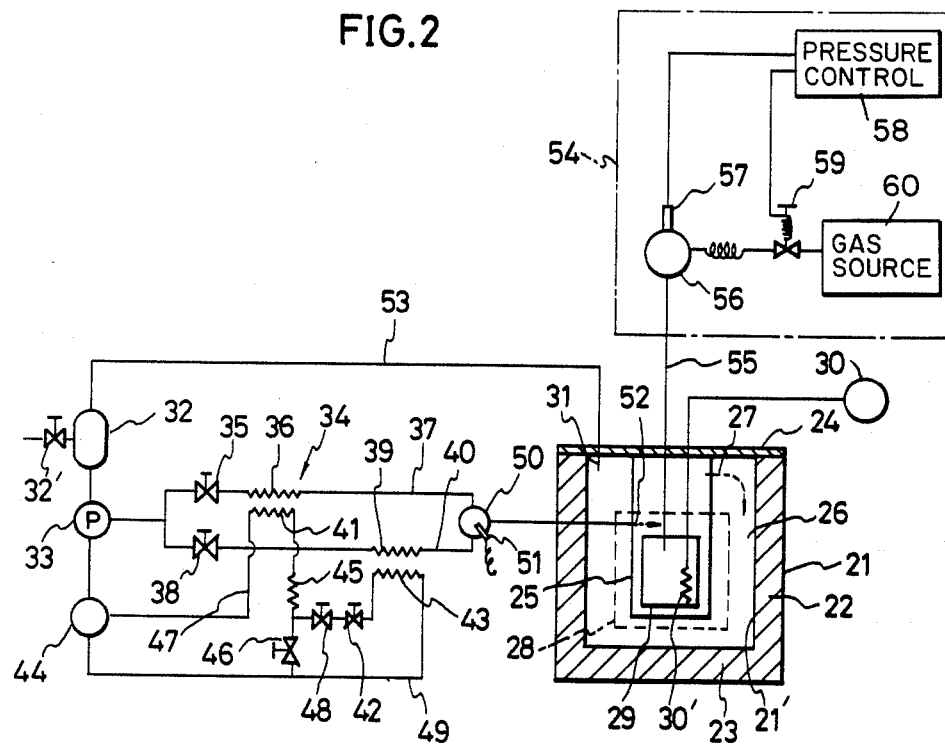
FIG. 2 is an explanatory piping diagram partly cut out of one preferred embodiment of an apparatus for measuring the melting point and the boiling point of gas constructed according to the present invention.

Reference is now made to the drawings, particularly to FIG. 2, which shows one preferred embodiment of an apparatus for measuring the melting point and the boiling point of gas constructed according to the present invention, and which is fundamentally similar to the structure shown in FIG. 1. In FIG. 2, reference numeral 21 designates a heat insulating tank. A heat insulating part 23 formed of a vacuum layer and a heat insulating material and so forth is formed at the body 22 of the tank 21. Reference numeral 24 indicates a cover of the tank 21. An inner tank 25 is internally provided within the tank 21. A passage 26 is interposed to flow heat medium as gas which will be hereafter described in greater detail, between the inner tank 25 and the inner wall 21' of the tank 21. A port 27 provided at the upper part of the tank 25 communicates between the tank 25 and the passage 26, and a radiation shield 28 is provided outside the inner tank 25.

A sample cell 29 is contained within the inner tank 25 and contains sample gas to be measured for the melting point and the boiling point thereof, and a temperature measuring system 30 for measuring the temperature of the gas is attached to the sample cell 29 and externally led.

The temperature measuring system 30 may employ a reference resistance thermometer in which a reference resistor 30' is internally mounted in the sample cell 20. Reference numeral 31 shows an output of the passage 26 provided at the cover 24.

Reference numeral 32 illustrates a heat medium source in which helium or the like is filled as the heat medium and to which a piping system 34 is connected through a circulation pump 33. The piping system 34 consists of a heating pipe route 37 having a heating flow rate control valve 35 manually or automatically controlled by a solenoid valve or the like and a heating heat exchanger 36 heated by a piping system 34 connected in series with the control valve 34, and a cooling passage 40 having a cooling flow rate control valve 38 and a cooling heat exchanger 39 connected in series with the control valve 38 as connected in parallel.

Figure 3:
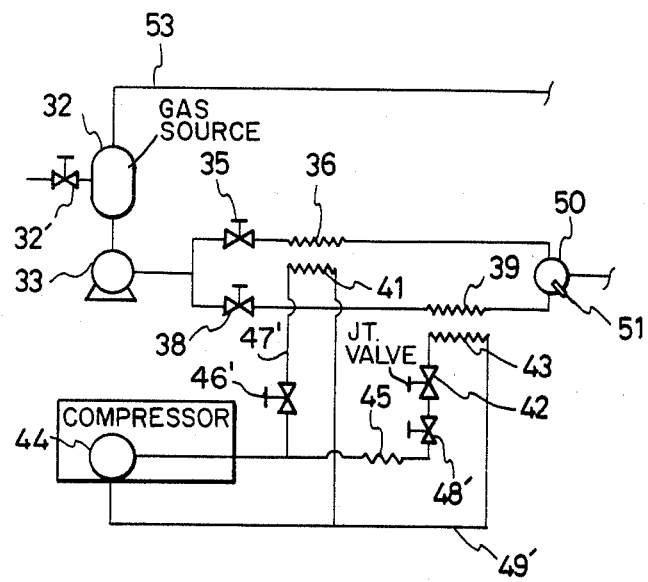
FIG. 3 is an explanatory piping diagram of essential part of another preferred embodiment of the apparatus of the invention.

In the above-described embodiment, the heating source and the cooling source for heating or cooling the heat exchanger 36 and 39 are not separately provided, but a heating part 41 such as a zigzag tube for heating the heat exchanger 36 is connected in series with a Joule-Thomson expansion valve 42, which will be hereinafter called "J-T expansion valve", and a cooling part 43 such as a zigzag tube for cooling the heat exchanger 39 is connected in series with a compressor 44 for compressing and supplying refrigerant such as Freon as shown in FIG. 2 or is connected in parallel with the compressor 44 as shown in FIG. 3.

More particularly, in the embodiment shown in FIG. 2, a heating pipe 47 which is connected in series with the heating part 41, a condenser 45 and a solenoid valve 46, is connected to the compressor 44, and a cooling pipe 49 which is connected in series with a solenoid valve 48, the J-T expansion valve 42 and the cooling part 43 is connected in parallel with the valve 46.

On the other hand, in the embodiment shown in FIG. 3, a heating pipe 47' which is connected in series with a solenoid valve 46' and the heating part 41, and a cooling pipe 49' which is connected in series with the condenser 45, a solenoid valve 48', the J-T expansion valve 42 and the cooling part 43 are respectively connected in parallel with the compressor 44.

In both embodiments, the heating part 41 is heated by the high pressure gas refrigerant which is supplied from the compressor 44 by the operations of the solenoid valves 46, 48, 46', 48', and the refrigerant is pressurized and liquefied by the codenser 45, the liquefied refrigerant is, in turn, adiabatically expanded by the J-T expansion valve 42, thereby lowering the temperature and cooling the cooling part 43 with the refrigerant, the refrigerant is then returned to the compressor 44, and is again compressed and supplied in a circulating system.

However, in the configuration shown in FIG. 2, the heating part 41 is always heated by the operation of the compressor 44.

On the other hand, in the configuration shown in FIG. 3, the heating part 41 and the cooling part 43 are selectively heated or cooled by the operations of the solenoid valves 46' and 48'.

In FIGS. 2 and 3, reference numeral 50 designates a mixer which is internally contained in a temperature sensor 51 provided in the outlet side joint of the piping system 34.

The outlet 52 of the piping system 34 is passed through the tank 21, and is opened at the upper part of the sample cell 20 in the tank 25.

Further, in the embodiment shown, the outlet 31 of the passage 26 is not opened at the exterior, but is connected through a return passage 53 to the heat medium source 32 such as tank for recovering the heat medium.

In addition, reference numeral 54 depicts a pressure regulator which communicates with the sample cell 29 for maintaining the internal pressure in the cell 29 constant or at desired internal pressure. In the embodiment shown, a pressure sensor 57 is provided at a pressure regulating tank 56 which communicates with the cell 29 and a capillary tube 55 in such a manner that the degree of opening of a gas flow regulating valve 59 is regulated by a pressure controller 58, to which the output of the sensor 57 is applied, thereby controlling the gas flow rate fed from the gas source 30 for containing pressure controlling gas to the tank 56 from a gas source 60.

When the sample gas in the cell 29 is in gas phase, the heat medium which passes through the heat exchanger 36 of the passage 37 is heated by the heating part 41 by flowing out the heat medium from the heat medium source 32 by the drive of the circulation pump 33 by regulating the opening of the valves 35, 38 and 48, the heat medium passed through the heat exchanger 39 of the passage 40 is cooled by the cooling part 43. In this manner, both the heat media are mixed by the mixer 50, and the temperature is detected by the sensor 51, and the heat medium cooled to the predetermined temperature is discharged from the outlet 52 of the piping system 34 into the tank 25.

As described above, the sample cell 29 contained in the tank 25 is cooled by the cooling medium thus discharged, thereby lowering the temperature of the sample gas, and the cooling medium is returned through the port 27, the passage 26, the outlet 31 and the return passage 53 to the heat medium source 32 for reuse.

Figure 4:
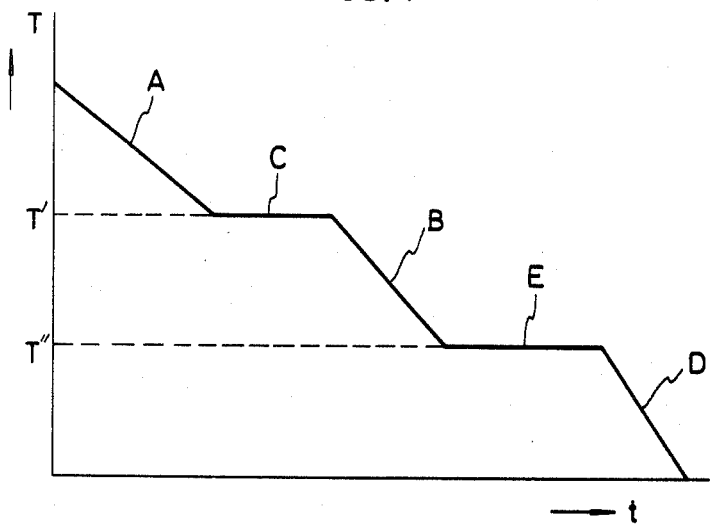
FIG. 4 is a graph indicating the temperature T of the sample gas with respect to the time t of the case where the melting point and the boiling point of the gas are measured by the apparatus of the invention.

In this manner, the sample gas of gas phase is cooled, the flow rate of the heat medium is controlled by the valves 35 and 38, thereby lowering the temperature of the gas as shown in FIG. 4. Then, when the medium is altered from the state of gas phase A to the liquid phase B, even if the temperature of the medium is lowered, the temperature of the sample gas is maintained by latent heat at the constant temperature state C. When the temperature of the sample gas of the state C is read by the temperature measuring system 30, the boiling point T' of the gas can be obtained.

When the temperature of the medium is lowered to the temperature in the vicinity of the boiling point T', the flow rate of the heat medium is actually slowly controlled by the valve 38 so that the temperature change of 0.1° C. per 10 to 20 min. occur, thereby accurately obtaining the boiling point T' which is at a constant temperature.

Then, when the medium of the liquid phase B is further cooled to lower temperature under the control, the constant temperature state E is presented before the medium becomes the state of solid phase D, thereby measuring similarly the melting point T''.

Further, when the sample gas is in solid phase D or in liquid phase B, the temperature of the sample gas can be raised by closing the valves 38 and 48 and opening the valves 35 and 46, thereby producing the reverse phase change to the above variation of state and measuring the melting point.

It is noted that, when the pressure regulator 54 is provided, it is preferred to employ the same pressure control gas as the sample gas.

According to the present invention as described above, since the apparatus for measuring the melting point and the boiling point of gas in which the inner tank 25 is provided via the passage 26 of the heat medium between the heat insulating tank 21 and the inner wall 21', the sample cell 29 having the temperature measuring system 30 of the sample gas is contained in the tank 25, the heating passage 37 which is connected in series with the valves 35 and 36, and the cooling passage 40 which is connected in series with the cooling flow rate control valve 38 and the cooling heat exchanger 39 are connected in parallel with the heat medium source 32 through the piping system 34, the outlet 52 of the piping system 34 is opened in the tank 25, the tank 25 communicates with the passage 26, and the outlet 31 of the passage 26 is provided in the tank 21, thereby measuring the melting point and the boiling point of the gas, wherein the heating part 41 for heating the heat exchanger 36 and the Joule-Thomson expansion valve 42 are connected in series with each other, and the cooling part 43 for cooling the heat exchanger 39 is connected in series with or in parallel with the compressor 44 for compressing and supplying refrigerant such as hydrocarbon fluoride, e.g. Freon ®, the temperature of the sample gas can be raised or lowered to the desired temperature by controlling the opening of the valves 36 and 38, and since the temperature change can be finely adjusted, the melting point and the boiling point of the gas can be accurately measured in response to the phase state of the sample gas, and yet since in the present invention the heat sources of the heat exchanger 36 and 39 are not separately provided but the heating and cooling sources are integrated in one pipe, the apparatus can be simplified, thereby reducing the cost.

Figure 5:
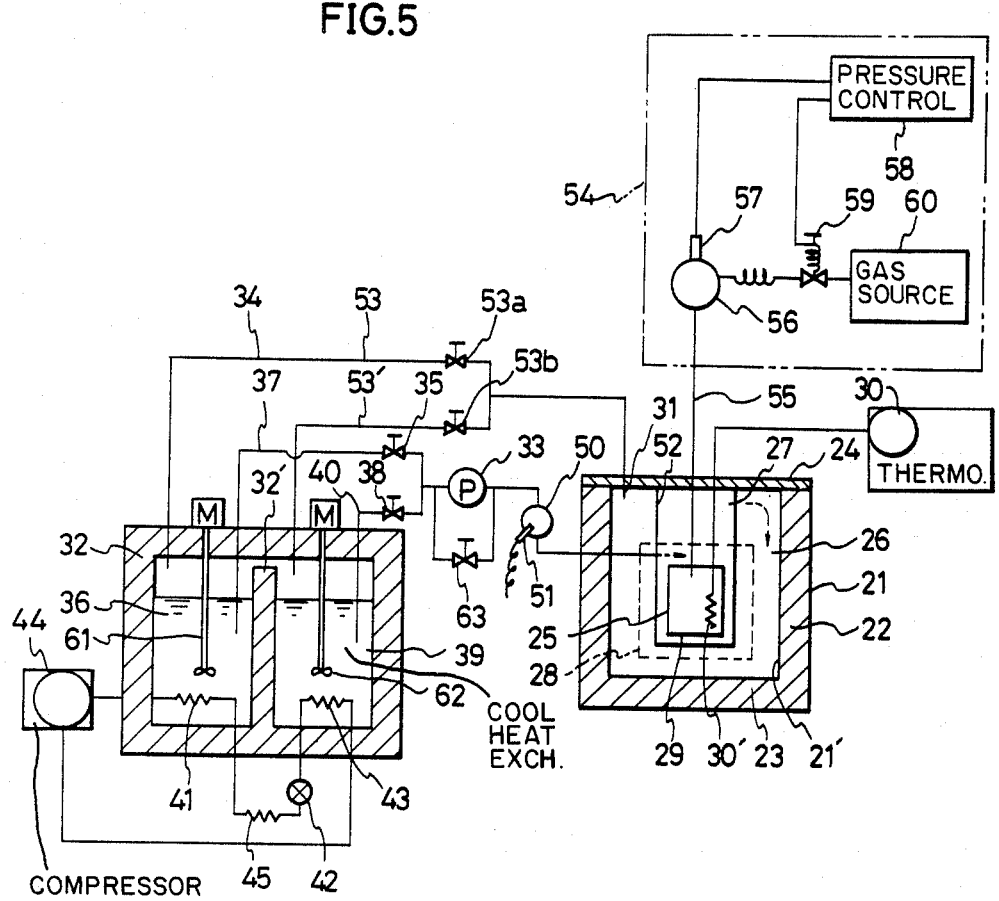
FIG. 5 is an explanatory piping diagram showing still another preferred embodiment of the apparatus for measuring constructed according to the present invention.

FIG. 5 shows another preferred embodiment of an apparatus for measuring the melting point and the boiling point of gas according to the present invention, wherein the like reference numerals designate the same or equivalent parts and units in FIGS. 2 and 3, and the difference of this embodiment from the first embodiment resides in the heat medium source 32 and its configuration.

More particularly, the heat medium source 32 in the previous embodiment stores gas as heat medium in the tank and the gas is used, while in the heat medium source shown in FIG. 5, a constant temperature tank is employed as a body of the heat medium source 32, in which a bank 32' provided at the intermediate of the tank communicate with each other at the upper part, and liquid of refrigerant such as hydrocarbon fluoride, e.g. Freon ® is contained in the space which is partitioned to the right and left compartment, thereby forming a heating heat exchanger 36 and a cooling heat exchanger 39 in such a manner that agitators 61 and 62 dipped in the liquid heat medium are rotatably driven by motors M.

Similar to the structure shown in FIG. 2, the heat exchanger 36 and the heat exchanger 39, and the tank 21 are connected via a piping system 34, at which a circulation pump 33 is interposed, a pump 33 which is connected in parallel with a bypass valve 63 is connected through a heating flow rate control valve 35 and a cooling flow rate control valve 38 to the heating and cooling passages 37 and 40 of pipes dipped in the heat medium of liquid in the exchangers 36 and 39, the outlet side is opened at the outlet 52 for controlling the temperature of the sample cell 29 through the mixture 50, pipes 53, 53' are respectively arranged in parallel through return control valves 53a, 53b from the outlet 31 opened with the passage 26 as shown in FIG. 5, and are provided at the gas phases of the heat exchangers 36 and 39, thereby constructing a circulating system.

Further, even in the second embodiment, the heating and cooling sources for heating and cooling the heat medium are not separately provided, but the heating part 41, a condenser 45, a Joule-Thomson expansion valve 42, and cooling part 43 are sequentially connected in series with the compressor 44 for compressing and supplying refrigerant such as Freon.

The heat medium of the heat exchanger 36 is heated by the heat of the heating part 41 of high pressure gas refrigerant supplied from the compressor 33, and is pressurized and liquefied by the condenser 45, and the liquefied heat medium is, in turn, adiabatically expanded by the expansion valve 42, thereby lowering the temperature and cooling the cooling part 43 and cooling the heat medium of the heat exchanger 39 as a circulating system.

Similar to the first embodiment, a temperature sensor 51 is internally contained in the mixture 50 provided with the outlet side joint of the piping system 34, and the outlet 52 of the piping system 34 is opened at the upper part of the sample cell 29 in the tank 25 through the tank 21.

When the sample gas in the sample cell 29 is in gas phase A in FIG. 4, the liquid refrigerant such as hydrocarbon fluoride, e.g. Freon ® of the heat exchanger 39 is cooled in advance by the cooling part 43 via the compressor 44 and the J-T expansion valve 42, the cooled refrigerant is, in turn, discharged into the tank 25 by opening the cooling passage 40 and the valve 38 and operating the circulation pump 33.

Thus, the sample cell 29 contained in the tank 25 is cooled with the cooling medium of liquid thus discharged, thereby lowering the temperature of the sample gas and measuring the boiling point of the gas.

The cooling medium is returned through the port 27, the passage 26, the outlet 31 and the return passage 53' to the state B.

Further, when the sample gas is in solid phase as shown in FIG. 4, the Freon 113 of the heat exchanger 36 is heated by the heating part 41, thereby gradually raising the temperature, producing reverse phase change to the previous change of state, and measuring the melting point of the gas.

When both the heat exchangers 36 and 39 are used in mixture by regulating the degree of openings of the valves 35 and 38, fine temperature change such as 0.1° C. per 10 to 20 min. can be produced in the same manner as in the case shown in FIG. 2, thereby more accurately measuring the boiling point and the melting point of the gas at the constant temperatures.

According to the apparatus for measuring the melting point and the boiling point of gas in accordance with the present invention as described above, sice in the heat medium source 32 in the first embodiment, the interior is partitioned via the bank 32' into the heat exchanger 36 and the heat exchanger 39 in the constant temperature tank, in which the heating part 41 for heating the heat medium of the liquid of the heat exchanger 36, the Joule-Thomson expansion valve 42, the cooling part 43 for cooling the heat medium of liquid of the heat exchanger 39, the compressor 33 for compressing and supplying the refrigerant such as Freon, and the condenser 45 are connected in series with each other, the heat media of the heat exchangers 36 and 39 are freely flowed from the outlet 52 through the pipes 37 and 40 having the valves 35 and 38, while the return piping system in which the return control valves 53a, 53b are interposed at the pipes 53, 53' are connected in parallel with the outlet 31 of the passage 26 of the heat medium is formed, and the tank 32 communicates with the passage 26 through the piping system, the temperature of the sample gas can be raised or lowered by controlling the openings of the valves 35 and 38, and the temperature change can be finely adjusted, the melting point and the boiling point can be accurately measured in response to the phase state of the sample gas, and yet since the heat exchangers 36 and 39 are not separately provided but are integrated in one constant temperature tank 32 of heat medium source in gas phase communicating state, the apparatus can be simplified and yet the gas can be cooled with the liquid having large thermal capacity, and the measuring time can be largely shortened efficiently.

It is to be observed therefore that to operate the apparatus of the present invention, sample gas supplied from a gas source 60 is introduced into a sample cell 25 of a heat insulating tank 21. The sample gas is then either heated or cooled in the cell by way of a heating heat exchanger 36 or a cooling heat exchanger 39, integrally installed in a heat insulating tank 21.

When the transition melting and/or boiling points of a gas are reached, the temperature is indicated by the thermometer connected to a sample gas measuring system 30.

What is claimed is:

1. An apparatus for measuring the melting point and the boiling point of gas, comprising:
   (a) a heat insulating tank (21) with an inner wall (21') also a heat medium passage (26) between said heat insulating tank (21) and said inner wall (21');
   (b) an inner tank (25) provided with said heat medium passage (26) between said heat insulating tank (21) and said inner wall (21');
   (c) a sample cell (29) contained within said inner tank (25) with a sample gas temperature measuring system (30);
   (d) a piping system (34) having a heating route (37) including a heating flow rate control valve (35) and a heating heat exchanger (36) heated by a heating source (32) connected in series with said control valve and a cooling route (40) including a cooling flow rate control valve (38) also a cooling heat exchanger (39) connected in series with said cooling flow rate control valve, said components being connected in parallel, and, including an outlet (52) of said piping system (34) opened within said inner tank (25), said inner tank (25) being communicated with said heat medium passage (26) and the output (31) of said heat medium passage (26); said apparatus being characterized in that
   (e) the heating of said heat exchanger (36) is also accomplished by means of a heating part (41) connected in series with a Joule-Thomson expansion valve (42), and there is a cooling part (43) for cooling said cooling heat exchanger (39) connected with a compressor (44) for compressing and supplying a refrigerant, whereby, a sample gas supplied from a gas source is introduced into a sample cell (25) of said heat insulating tank (21), said sample gas being then heated or cooled in the cell by means of a heating heat exchanger (36) or a cooling heat exchanger (39), when the transition melting and/or boiling points of the sample gas are reached, the temperature is indicated by a thermometer connected to the sample gas measuring system.

2. An apparatus as claimed in claim 1 wherein said cooling part (43) is connected in series with a compressor.

3. An apparatus as claimed in claim 1 wherein said cooling part (43) is connected in parallel with a compressor.

* * * * *